United States Patent
Zheng

(10) Patent No.: US 7,445,009 B2
(45) Date of Patent: Nov. 4, 2008

(54) SPATIAL FIELD EFFECT PHYSICAL THERAPY DEVICE

(76) Inventor: Jibing Zheng, Room 13-2, No. 8 Fucheng Road, Haidian District, Beijing (CN) 100830

( * ) Notice: Subject to any disclaimer, the term of this patent is extended or adjusted under 35 U.S.C. 154(b) by 732 days.

(21) Appl. No.: 10/501,055

(22) PCT Filed: Jan. 14, 2003

(86) PCT No.: PCT/CN03/00024

§ 371 (c)(1),
(2), (4) Date: Jul. 9, 2004

(87) PCT Pub. No.: WO03/059448

PCT Pub. Date: Jul. 24, 2003

(65) Prior Publication Data

US 2005/0076923 A1    Apr. 14, 2005

(30) Foreign Application Priority Data

Jan. 15, 2002  (CN) .......................... 02 2 00567 U

(51) Int. Cl.
*A61B 19/00*   (2006.01)
(52) U.S. Cl. .................................... 128/897
(58) Field of Classification Search .............. 600/13, 600/15; 607/2, 87, 88, 96, 104, 107, 109; 362/231, 555; 601/56, 57; 128/897, 898, 128/899

See application file for complete search history.

(56) References Cited

U.S. PATENT DOCUMENTS 5,607,631 A * 3/1997 Wolfson et al. ............. 264/138
2004/0081948 A1 * 4/2004 Goodwin .................... 434/258

FOREIGN PATENT DOCUMENTS

| CN | 1089817 | 7/1994 |
| CN | 1276201 | 12/2000 |
| CN | 2461530 | 11/2001 |

* cited by examiner

*Primary Examiner*—Charles A. Marmor, II
*Assistant Examiner*—Aaron B Colquitt
(74) *Attorney, Agent, or Firm*—McDonnell Boehnen Hulbert & Berghoff LLP

(57) ABSTRACT

A spatial field effect physical therapy device including a base and 64 equidistant Yijing columns fitted on the base in the form of a square by 8 rows and 8 columns, each Yijing column is at a height of 2 to 18 unit length, in the rectangle consisted of arbitrary 4 Yijing columns, the sums of the heights of the Yijing columns at the ends of each diagonal of the rectangle is equal to each other. This spatial field effect physical therapy device needn't an incoming energy and is able to cure pains in human body effectively.

12 Claims, 4 Drawing Sheets

SPATIAL FIELD EFFECT PHYSICAL THERAPY DEVICE

TECHNICAL FIELD

The present invention relates to a medical instrument, especially to a spatial field effect physical therapy device.

BACKGROUND OF THE INVENTION

At present, there are many kinds of field effect medical instruments in the market. All of them treat diseases for human being by means of incoming energy such as sound, light, electricity, magnetism or radiation. The curative effects of these instruments are different. In addition, some of them have influence on other tissues during the treatment and therefore bring adverse effects. Furthermore, the improper distribution of energy will also affect the curative effects.

SUMMARY OF THE INVENTION

The present invention provides a spatial field effect physical therapy device without using incoming energy, which can effectively treat diseases for human, especially can effectively ameliorate pain, local swelling and dysfunction. The spatial field effect physical therapy device is simple in structure, easy to use, safe and credible.

The spatial field effect physical therapy device according to the present invention comprises a base and 64 equidistant Yijing columns fitted vertically on the same in the form of a square array by 8 rows and 8 columns. Each Yijing column is at a height of 2-18 unit length. The sum height of two diagonal Yijing columns of a rectangle formed by any 4 columns in the square array is equal to that of the other two diagonal columns.

The Yijing columns at the four corners of the square array are higher than the others, respectively at the height of 16, 17, 18, and 17 unit length in the spatial field effect physical therapy device according to the present invention.

The space between two neighbouring Yijing columns is ⅓~½ of the Yijing column's diameter in the spatial field effect physical therapy device according to the present invention.

The Yijing columns of the spatial field effect physical therapy device according to the present invention are metal columns.

The Yijing columns of the spatial field effect physical therapy device according to the present invention are solid columns.

The Yijing columns of the spatial field effect physical therapy device according to the present invention are hollow columns.

The spatial field effect physical therapy device according to the present invention further comprises a transparent mask on the base which covers all the Yijing columns.

The spatial field effect physical therapy device according to the present invention is developed according to traditional Chinese medicine and Taiji Yin-and-Yang theory of Yijing. It forms radiation field with high energy through testing. Accordingly, it can cure various kinds of diseases in human body, especially has significant effect on the pains resulted from the diseases of cervical vertebra and lumbar vertebra, rheumatic and rheumatoid diseases.

PREFERABLE EMBODIMENTS OF THE INVENTION

The present invention will be described in more detail according to the figures and embodiments in the following.

Figure 1:
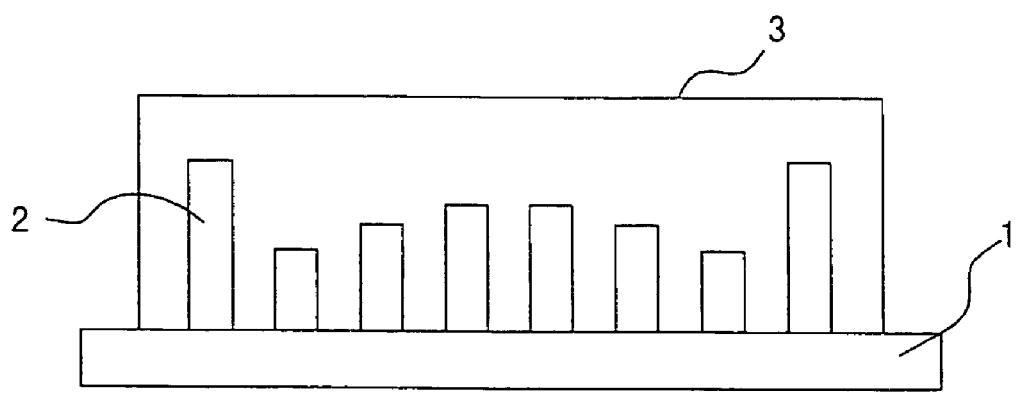
FIG. 1 is the sketch map of the spatial field effect physical therapy device according to the present invention.
Figure 2:
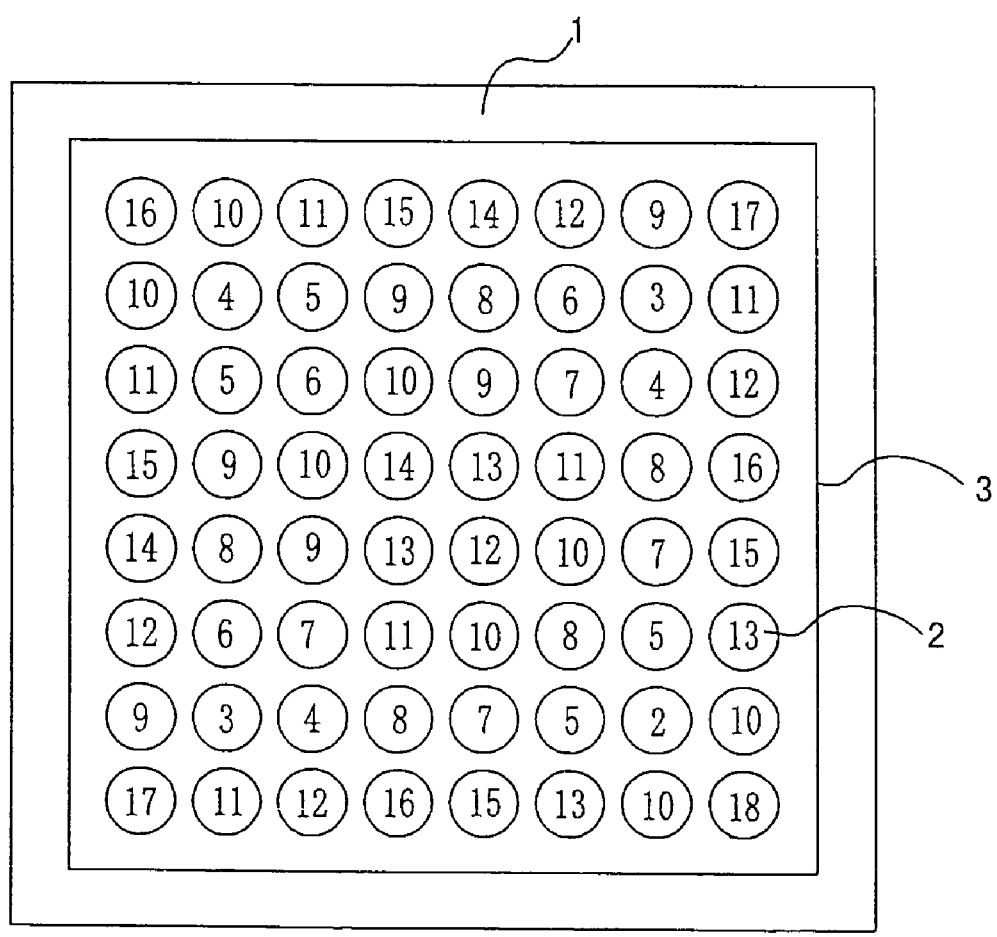
FIG. 2 is the ichnography of the spatial field effect physical therapy device according to the present invention.

The spatial field effect physical therapy device (see FIG. 1 and FIG. 2) comprises base (1), Yijing columns (2) and a transparent mask (3), said 64 Yijing columns (2) are vertically fitted on the base (1) in the form of a square array by 8 rows and 8 columns in equidistance, said mask is placed on the base and covers all the Yijing columns. Each Yijing column (2) is at a height of 2~18 unit length, and the Yijing columns at the four corners of the square are higher than others, respectively at a height of 16, 17, 18, and 17 unit length. Furthermore, the space between two neighbouring Yijing columns (2) is ⅓~½ of the Yijing columns' diameter. In FIG. 2, the numbers on the Yijing columns represent the relative heights of the columns, for example, number 10 means 10 unit length. The sum height of two diagonal Yijing columns of a rectangle formed by any 4 columns in the square array is equal to that of the other two diagonal columns, for example, 16+18=17+17, 9+9=14+4, 12+5=7+10, 5+10=6+9, 13+3=9+7, 16+5=11+10, 6+7=9+4, etc. The Yijing columns are solid metal columns.

Figure 3:
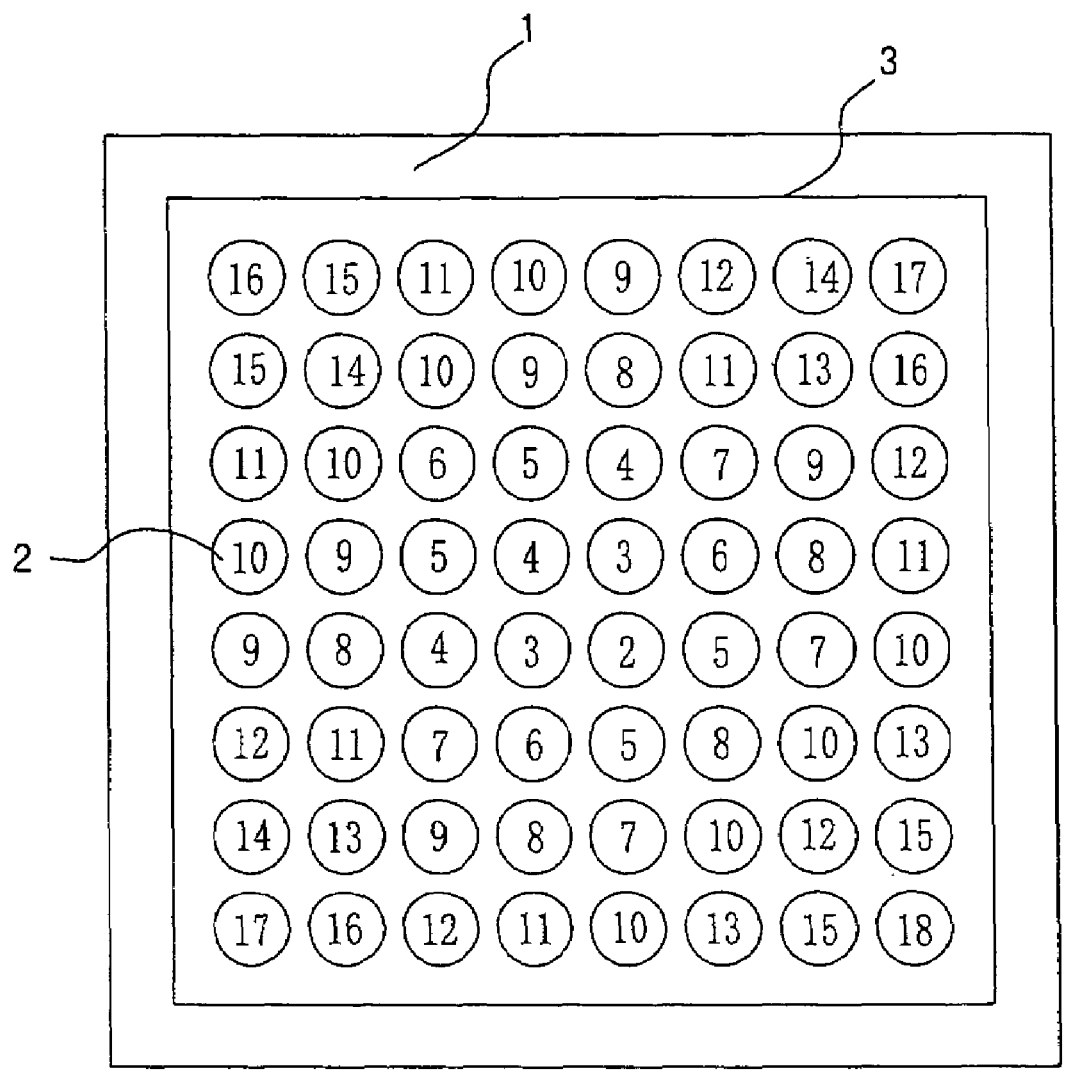
FIG. 3 is the ichnography of the spatial field effect physical therapy device in another embodiment according to the present invention.

Yijing columns of the spatial field effect physical therapy device can be arrayed in various styles. FIG. 3 is another style of arrangement, wherein the numbers on the Yijing columns represent the relative heights of the Yijing columns. Advantageously, the style of arrangement in FIG. 2 can achieve the best curative effects.

The Yijing columns of the spatial field effect physical therapy device can be made of metal, or other materials. They can be solid or hollow columns. Advantageously, the spatial field effect physical therapy device with the solid metal Yijing columns can bring better curative effects.

The device is placed in contraposition to the sites of pain or pathologic changes when used, and the distance between body surface and the device is 0~50 cm, preferably 10~30 cm. The spatial field effect physical therapy device can be mono-used with Yijing columns facing to body upside down. Alternatively, the device can also be used in pairs oppositely positioned, between which the human body is in the middle, and thus can achieve better effects.

INDUSTRIAL APPLICABILITY

The spatial field effect physical therapy device according to the present invention used as a medical instrument can achieve curative effects on many diseases in human body, e.g. trauma, acute and chronic soft tissue injury, sequela of cerebrovascular lesion, pelvic inflammation, periarthritis of shoulder, and urinary system infection, etc, especially has prominent effect on the pains of cervical vertebra and lumbar vertebra diseases, rheumatic and rheumatoid diseases.

The Studies for the Functions and Effects of the Spatial Field Effect Physical Therapy Device The experiments of studying for the functions of the device are as follows:

I. The Energy Density Distribution of the Radiation Field Formed by the Yijing Columns Array is Measured by Infrared Thermal Image Device.

Apparatus for testing: Thermal Image System, model TVS-5500

Samples for testing: two sets of copper Yijing columns, one is long columns array, and the other is short columns array.

Testing methods: the long Yijing columns are arrayed in different styles, which are then tested respectively. While, the short Yijing columns are arrayed in one style for testing twice.

Results of testing: as shown in Tab. 1

TABLE 1 image data of the radiation field formed by the Yijing columns array measured by thermal image device

| thermal image Number | sample for testing | radiation temperature (° C.) |
|---|---|---|
| 11251 | Long columns, 8 × 8, randomly arrayed | 10-30 |
| 11252 | Short columns, 8 × 8, regularly arrayed | 10-30 |
| 11253 | Long columns, 8 × 8, randomly arrayed | 18-23 |
| 11254 | Long columns, 8 × 8, randomly arrayed | 20-24 |
| 11255 | Long columns, 4 × 4, regularly arrayed | 20-24 |
| 11256 | Long columns, 6 × 6, regularly arrayed | 20-24 |
| 11257 | Long columns, 8 × 8, regularly arrayed | 20-24 |
| 11258 | Long columns, 8 × 8, regularly arrayed | 20-24 |
| 11259 | Short columns, 8 × 8, regularly arrayed | 20-24 |
| 11260 | Long columns, 8 × 8, regularly arrayed | 20-24 |

Analysis of the testing results: Infrared radiation energy is expressed by radiation temperature value of each point of the thermal image is radiation temperature $T_Y$, which reflects the radiation energy density $E_Y$ of the region containing the point. The relationship is:

$$E_Y = \sigma T_Y^4$$

wherein, $\sigma$ is Stefan-Boltamann Constant $5.68 \times 10^{-8} Wm^{-2}K^{-4}$ $T_Y$ is the sum of the temperature t showed on the image and 273, i.e., $$T_Y = t + 273 (K)$$

The value of the temperature showed on the thermal image reflects the amount of radiation energy density.

Figure 4:
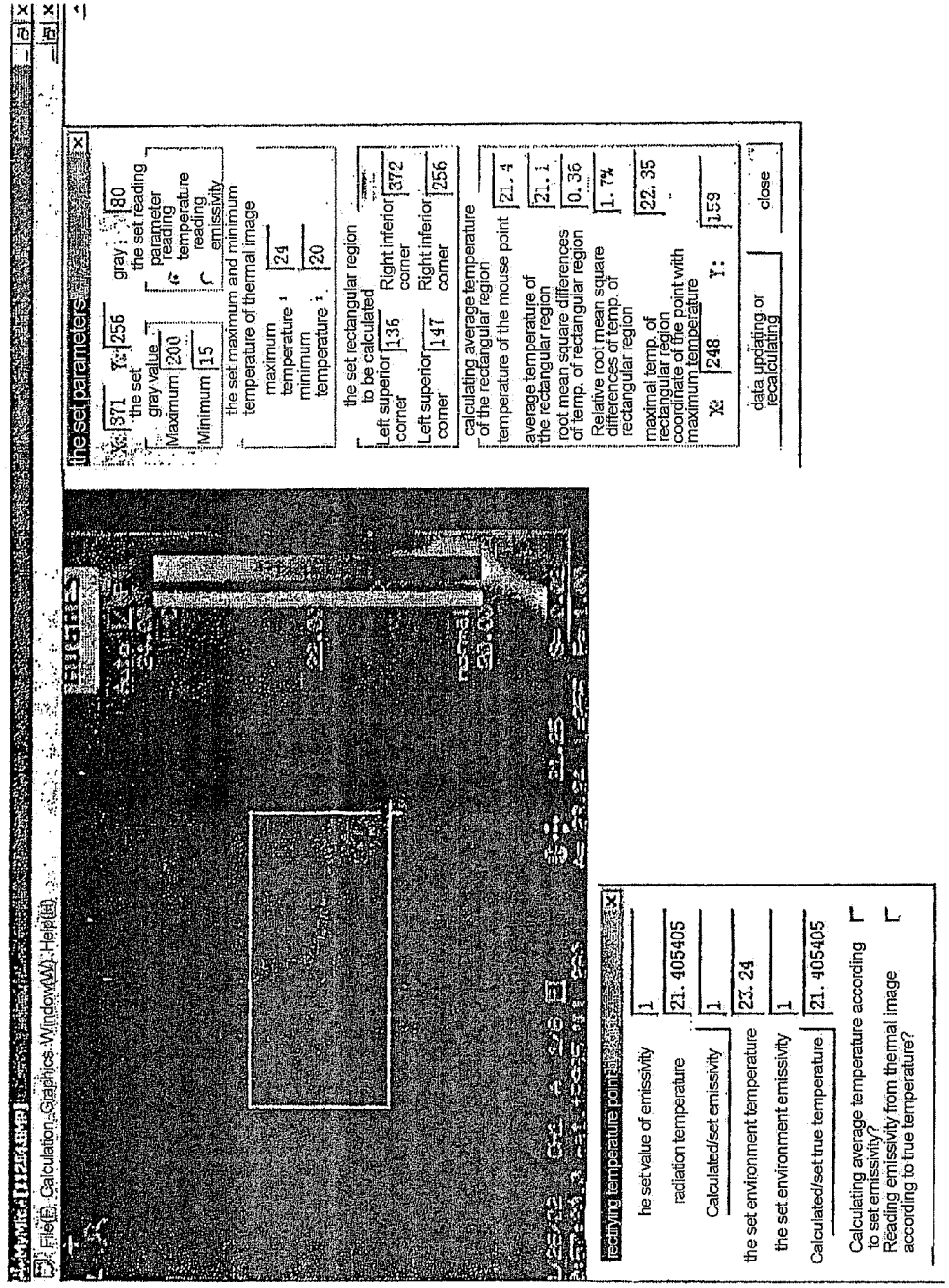
FIG. 4 shows data processing for infrared thermal image No. 11254.
Figure 5:
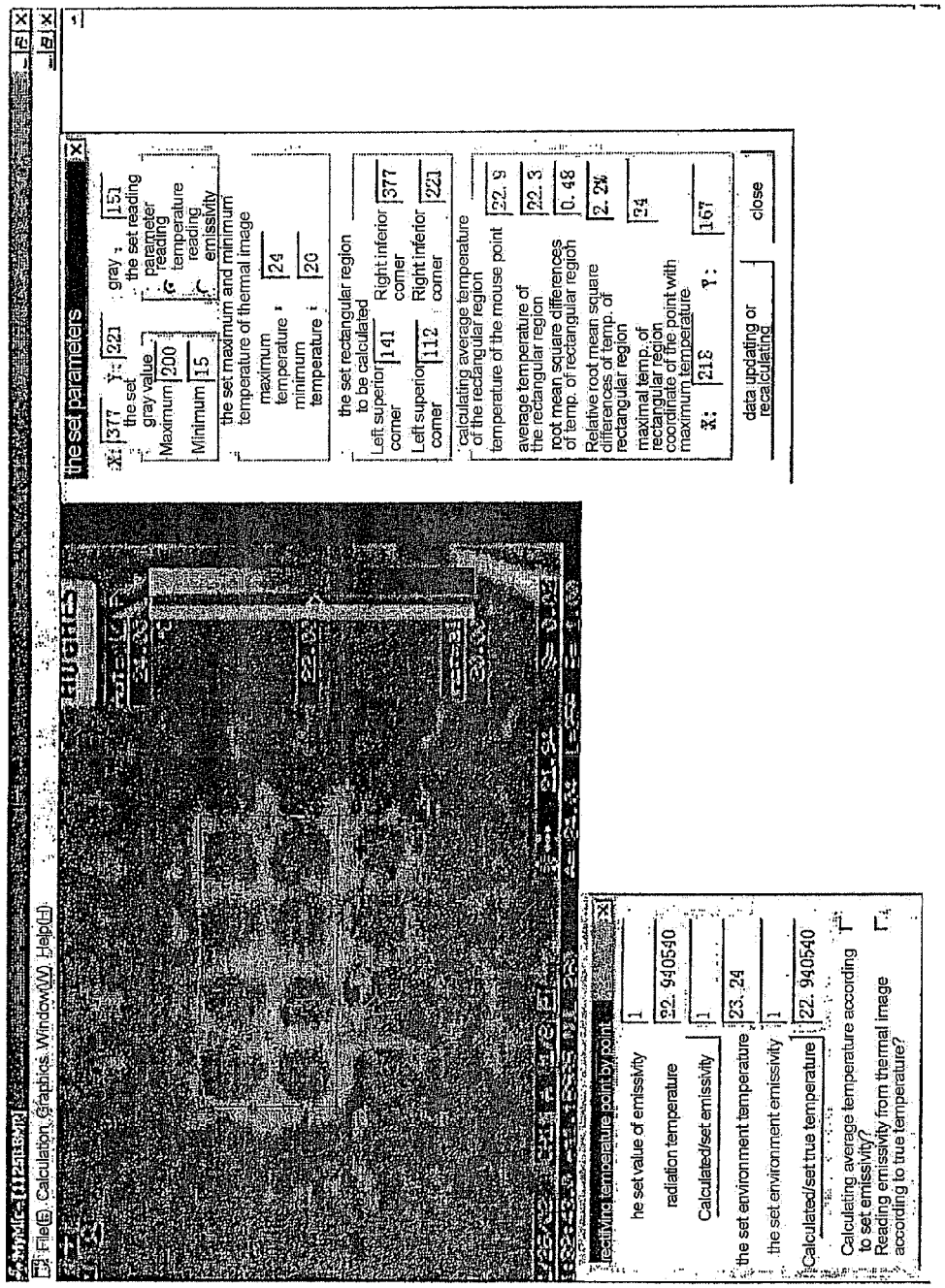
FIG. 5 shows data processing for infrared thermal image No. 11258.

The value of the radiations formed by the Yijing columns arrays in different styles of arrangement, the data of infrared thermal images are processed with computer software. FIG. 4 is the interface of the software for processing infrared thermal image, in which image of No. 11254 is being processed. The dialog box on the left upper part is the set value of emissivity. The gray value and the maximal or minimal temperature can be read directly from the thermal image. FIG. 5 shows the processed result for image of No. 11258. In order to test the effects of radiation field formed by the Yijing columns array, it is needed to obtain the temperature field which is a region with higher temperature formed by the Yijing columns array. Next, evaluate the energy of the radiation field formed by the Yijing columns array based on the average radiation temperature and the maximal radiation temperature of this region. For this purpose, the emissivity of all the regions for testing are set as 1. A rectangle pane is selected in the region with higher temperature for each thermal image obtained from the test. The pane is a circumscribed rectangle of 4×2 copper columns with the scope of 136×109 in the image. Calculating the average radiation temperature and the maximal radiation temperature of each rectangle, and then comparing the processed data of the infrared thermal images corresponding to the different styles of arrangement. The results are shown in Tab. 2. Tab. 2 shows the processed data of image No. 11258.

TABLE 2 processed data of the thermal images

| thermal image number | sample for testing | Room temperature when testing (° C.) | Average temperature of the rectangle region (° C.) | Root mean square differences of temperatures in rectangle region (° C.) | Relative root mean square differences of temperatures in rectangle region (° C.) | Maximal temp. in the rectangle region (° C.) |
|---|---|---|---|---|---|---|
| 11251 | Long columns, 8 × 8, randomly arrayed | 22.14 | 20.0 | 0.63 | 3.2 | 21.61 |
| 11252 | Short columns, 8 × 8, regularly arrayed | 22.34 | 17.4 | 2.13 | 12 | 21.29 |
| 11253 | Long columns, 8 × 8, randomly arrayed | 22.84 | 20.8 | 0.36 | 1.8 | 22.05 |
| 11254 | Long columns, 8 × 8, randomly arrayed | 23.24 | 21.1 | 0.36 | 1.7 | 22.35 |
| 11255 | Long columns, 4 × 4, regularly arrayed | 23.64 | 21.9 | 0.47 | 2.1 | 23.39 |

TABLE 2-continued processed data of the thermal images

| thermal image number | sample for testing | Room temperature when testing (° C.) | Average temperature of the rectangle region(° C.) | Root mean square differences of temperatures in rectangle region(° C.) | Relative root mean square differences of temperatures in rectangle region(° C.) | Maximal temp. in the rectangle region(° C.) |
|---|---|---|---|---|---|---|
| 11256 | Long columns, 6 × 6, regularly arrayed | 23.74 | 22.1 | 0.46 | 2.1 | 23.78 |
| 11257 | Long columns, 8 × 8, regularly arrayed | 23.94 | 22.1 | 0.46 | 2.1 | 23.65 |
| 11258 | Long columns, 8 × 8, regularly arrayed | 24.04 | 22.3 | 0.48 | 2.2 | 24 |
| 11259 | Short columns, 8 × 8, regularly arrayed | 24.14 | 20.7 | 0.81 | 3.9 | 22.51 |
| 11210 | Long columns, 8 × 8, regularly arrayed | 24.14 | 22.4 | 0.54 | 2.4 | 24.04 |

It is concluded from the above table that the data of images No. 11254 and 11258 is obviously different with each other. Both of them are copper long columns arrayed by 8×8, temperature ranging 20~24° C., with 0.8° C. difference of room temperatures, 1.2° C. difference of average temperature of the rectangle region, 1.65° C. difference of maximal temperature when testing. It can be observed from the thermal images that the root mean square differences of temperature are caused by the lower radiation temperature of the copper columns and higher radiation temperature of the interspacing region. The root mean square difference of No. 11258 image is higher than that of No. 11254 image, which indicates that the temperature of the interspacing region of No. 11258 image increases comparing with that of No. 11254 image. It can be concluded from the above test that the radiation field formed by the regularly arrayed columns has higher energy than that of the randomly arrayed columns.

II. Experiments for the Influence of the Yijing Columns on the Growth of Bacteria and Moulds a. First add culture medium into culture plates, and then put the plates as samples over the Yijing columns array, and the plates as controls in the normal conditions. After several days, it was observed that moulds grew in the sample plates, while no moulds grew in the control plates.

b. First inoculate *Escherichia coli* onto the inclined plane of the test tubes, and then put the test tubes as samples over the Yijing columns array, and the test tubes as controls in the normal conditions. After several days, it was observed that bacteria on the inclined plane of samples 1, 3 grew much better than those of controls 2, 4.

III. Experiment for Enhancing Hypoxia Tolerance of Mice by the Yijing Columns Array Experiment methods: in conformity with the examination method for the function of hypoxic tolerance prescribed by "Examination Method and Evaluation Procedure for Functionology of Health Food" issued in 1996 by the Ministry of Health.

Experimental animals: male Kunming mice, grade 2, about 6 weeks old, with the body weight of 20~24 g (22.7±1.86 g), purchased from the Breeding Group in Institute of experimental animal, Chinese Academy of Medical Sciences, with the Certificate No. 01-3001.

Grouping and feeding for animals: after two days of adaptation in the animal laboratory, 60 experimental animals were randomly divided into 2 control groups and 2 experimental groups according to their body weights, 15 animals per group. Animals in each group were fed with normal animal feeds and drink freely.

Experiment Procedures:

The experimental animals were placed on the experimental frame. The Yijing columns were put right under the experimental frame. The control groups were placed on the experimental frame with the same height which was put in the normal conditions. Furthermore, the distance between experimental groups and control groups is more than 3 meters.

The experiment of hypoxic tolerance under normal pressure proceeded at two stages. The mice were bred for 14 days at the first stage, and 30 days at the second stage. Then the experiment of hypoxic tolerance under normal pressure was conducted respectively on the above mice.

Put mice of each group into 250 ml jars with 15 g soda-lime per jar, and the jar mouths were smeared with Vaseline, only one mouse in each jar. Immediately cover the lids to make the jar airtight as soon as the mice were put in. Subsequently record the duration time till the mice's breath cease.

Statistical analysis: H analysis (Kruskal-Wallis One Way Analysis of Variance on Ranks) being used for statistical analysis.

Results: results in the following table are the duration time of the control and experimental groups under the normal pressure hypoxia conditions. For the mice at first stage of treating for 14 days, the duration time of experimental group 1 has the tendency of prolonging by comparison with control group 1. For the mice at the second stage of treating for 30 days, the duration time of experimental group 2 increases averagely 3.2 minutes in comparison with control group 2, existing significant difference by statistical analysis.

Conclusions: the Yijing columns have the effects of enforcing hypoxic tolerance on mice.

TABLE 3

Effect of Yijing columns on the duration time of mice under the normal pressure hypoxia conditions

| Groups | Numbers of animals | Experimental period (day) | Hypoxia tolerance time (min) (x ± SD) |
|---|---|---|---|
| Control group 1 | 15 | 14 | 23.1 ± 2.83 |
| Exprerimental group 1 | 15 | 14 | 24.2 ± 4.55 |
| Control group 2 | 15 | 30 | 19.1 ± 2.55 |
| Experimental group 2 | 15 | 30 | 22.3 ± 3.17* |

Variance analysis:
*P < 0.05 as comparing experimental group 2 with control group 2.

IV. Experiment for Promoting White Wine Aging by the Yijing Columns

Hongxing-brand erguotou white wine of the same manufacture batch was divided into two groups. One group was placed between two opposite-positioned Yijing columns array, and another group was placed in the normal conditions. After 30 minutes, took 23 ml of white wine respectively as sample and control, and added 20 ml of dichloromethane for extracting. The following table 4 shows the analysis of gas chromatography-mass spectrometry for the fluid extraction.

TABLE 4

Analysis of gas chromatography-mass spectrometry for the fluid extract of Hongxing-brand erguotou white wine

| Component | Percentage in the sample (%) | Percentage in the control (%) |
|---|---|---|
| Propanol | 2.92 | 2.04 |
| Ethyl acetate | 62.01 | 64.28 |
| Acetic acid | 6.21 | 4.51 |
| Diethoxy ethane | 18.18 | 20.00 |
| Ethyl octanoate | 0.75 | 0.71 |
| Dimethyl butanol | 1.72 | 0.82 |
| ethyl Hydroxy-propionate | 3.76 | 2.95 |
| Ethyl palmitate | 0.78 | 0.52 |
| Ethyl oleate | 0.72 | 0.62 |

The white wine samples and the controls were placed respectively in the above conditions for 30 minutes, 60 minutes, 90 minutes and 120 minutes. There were different changes of the taste for the samples treated for different time tasted by the wine-tasting experts. The white wine samples treated within 90 minutes tasted more fragrant and gentle but less sweet, bitter and astringent. The white wine treated over 90 minutes tasted rough, hot, and more astringent. There was no change in the control group.

When placing the white wine into or within the scope of 5~20 meters around the large-scale Yijing columns array with the maximal height of 6.6 meters, the taste of the white wine also changed obviously after several tens of minutes. The change was much greater than the small-sized Yijing columns array. The distance around retaining effectiveness was much longer than the small-sized Yijing column array.

The inventor repeated many times of the experiments for Hongxing-brand erguotou white wine, all the components of the wine changed greatly.

V. Experiments for the Medical Effects of the Spatial Field Effect Physical Therapy Device The spatial field effect physical therapy device is a new type of curative instrument developed by Institute of Taiji Culture, Center for Situation in China, Peking University, according to traditional Chinese medicine, Taiji and Yin-and-Yang theory, with Yijing columns as its functional parts. 3 stages of clinical trials have been conducted respectively in October, 2001~January, 2002 and March, 2002~August, 2002. In stage I: the Yijing columns are aluminum hollow columns, un-heated, placed up and down opposite; In stage II: the Yijing columns are aluminum hollow columns, partially heated (in combination with ultra-infrared thermal-electrical radiation), placed up and down opposite; In stage III: the Yijing columns are aluminum solid columns, wholly heated (with the same method as in stage II), but the operating method is different with those in the two foregoing stages. The method in stage III is placing the device into mattress of bed to form 2 short-distance fields with cushion-shaped instead of placing under bed as a long-distance field in the two foregoing stages, and no change for the equipment over the patient.

When treating with the spatial field effect physical therapy device, the patient lay in bed, and two sets of Yijing columns were placed oppositely, one was under the bed and the other was over the patient's body. The effects were observed by comparison with the patient himself before treatment.

Stage I: Clinical trials of spatial field effect physical therapy device for treating pains of cervical vertebra disease, lumbar vertebra disease and rheumatic disease General statistics: 60 patients were randomly selected from clinic service, among which there were 30 with cervical vertebra and lumbar vertebra diseases, and 30 with rheumatic diseases. All of them were in conformity with the criteria for selection. Among the 30 patients with cervical vertebra and lumbar vertebra diseases, 9 were male and 21 were female with age of 37 to 75 years old, the average age was 57.7 years old; and among the 30 rheumatic disease patients, 2 were male and 28 were female with age of 20 to 75 years old, the average age was 51.63 years old.

Course of diseases of the patients:

| Groups | case numbers | ≦5 years N | (%) | ≦5 years N | (%) | >10 years N | (%) |
|---|---|---|---|---|---|---|---|
| cervical vertebra and lumbar vertebra diseases | 30 | 17 | 56.67 | 8 | 26.67 | 5 | 16.67 |
| Rheumatic disease | 30 | 17 | 56.67 | 5 | 16.67 | 8 | 26.67 |

Wherein, the longest course of cervical vertebra and lumbar vertebra diseases was 20 years, and the shortest was half a year, the average course was 6.05±5.45;

the longest course of rheumatic disease was 40 years, and the shortest was 2 months, the average course was 8.23±9.14.

Selection of Patients

I. Inclusion Criteria:

Patients with positive changes observed in cervical vertebra and lumbar vertebra by X-ray examination or patients with positive diagnosis of cervical vertebra and lumbar vertebra diseases or rheumatic disease;

II. Exclusion Criteria:

i. One of age <18 or >75 years old;

ii. One with the primary severe pathological changes in brain, kidney, respiratory system, or hematopoietic system;

iii. One with mental disorder or malignant tumor;

iv. Female in pregnancy or lactation period;

v. One who does not cooperate with the therapy.

Treatment method: the device was in contraposition to the sites of pain or pathologic changes, with the distance of 10~30 cm between the device and body surface. The device was used for 20 days as a course of treatment, once one day, 40 minutes every time. The curative effects were observed by comparison with the patient himself before treatment. During treated by the device, it was required to stop all the antipyretic and antalgic drugs and other kinds of treatments.

Observation of the Curative Effects:

I. Observe the amelioration of related symptoms and signs, and the onset time of taking effect on the main symptoms.

II. For the patients with rheumatic arthritis, conduct the tests for determining rheumatism (conduerythrocyte sedimentation rate test, anti-streptolysin "O" test and rheumatoid factor test) before and after the treatments (30 patients are tested).

III. Record the adverse reactions.

Criteria for the Grades of Diseases:

A. criteria for the grades of symptoms of cervical vertebra and lumbar vertebra diseases 1. criteria for the grades of pains:

Grade I: no obvious pain in stillness or in movement;

Grade II: feel tolerable pain in normal movement having no influence on daily activities;

Grade III: feel intolerable pain in stillness having influence on daily activities.

2. criteria for the grades of dysfunction:

Grade I: feel tired sometimes in the sites of pathologic changes, no pain during daily activities, assistance is required when changing posture, and diagnosis of dysfunction is negative;

Grade II: feel mild pain at the beginning of movement. The pain continues along with continuous movement, but disappears after rest. The movement of arthrosis or some local parts is slightly restrained;

Grade III: feel severe pain in movement, and the pain reduced somewhat in stillness, the movement is obviously restrained, swelling in local part or disfiguration of the arthrosis.

B. Criteria for the Grades of Pains in Rheumatism 1. tenderness in the joints:

Grade I: feel no tenderness, but feel tenderness during stress or maximum passive movement;

Grade II: feel tenderness during stress on the edge of the joints or touching the ligaments;

Grade III: feel tenderness and frown to express the feeling of pain during stress. The movement is slightly restrained;

Grade IV: feel severe tenderness during stress. The passive movement is severely restrained.

2. swelling:

Grade I: no swelling;

Grade II: slightly swelling, and clear apophysis nearby;

Grade III: the swelling is as high as the apophysis;

Grade IV: the swelling is higher than the apophysis which hinders the functions and activities of the joints.

3. Morning stiffness: record the duration time of morning stiffness.

4. Grasp force: the patients try their best to grasp and press 3 times the cuff of the hemomanometer charged gases to 20 mmHg respectively by the left and right hands. Record and average the values to obtain the grasp force of the two hands.

Criteria for Evaluating the Curative Effects:

1. recovery after clinical treatment: complete remission of the symptoms;
2. apparently effective: the grade of the symptoms is ameliorated with 2 grades or more than 2 grades after treatment;
3. effective: the grade of the symptoms is ameliorated with 1 degree after treatment;
4. noneffective: no amelioration of the symptoms after treatment.

Results of Treatment 1. curative effect on symptoms in cervical vertebra and lumbar vertebra diseases: shown in Tab. 5

TABLE 5

| | curative effect on symptoms in cervical vertebra and lumbar vertebra diseases | | | | | | | |
|---|---|---|---|---|---|---|---|---|
| Symptoms observed | Case numbers | recovery | | apparently effective | | effective | | Noneffective |
| | | N | (%) | N | (%) | N | (%) | N | (%) |
| Pain | 30 | 1 | 3.33 | 3 | 10 | 19 | 63.33 | 7 | 23.3 |
| Dysfunction | 10 | 0 | 0 | 3 | 30 | 7 | 70 | 0 | 0 |

2. curative effect on symptoms in rheumatism arthritis diseases: shown in Tab. 6

TABLE 6

| | curative effects on symptoms in rheumatism arthritis diseases | | | | | | | |
|---|---|---|---|---|---|---|---|---|
| Symptoms observed | Case numbers | recovery | | apparently effective | | effective | | Noneffective |
| | | N | (%) | N | (%) | N | (%) | N | (%) |
| Pain | 30 | 1 | 3.33 | 3 | 10 | 14 | 46.67 | 12 | 40 |
| Swelling | 23 | 1 | 4.35 | 0 | 0 | 10 | 43.48 | 12 | 52.17 |
| Morning stiffness | 27 | 2 | 7.4 | 2 | 7.4 | 11 | 40.74 | 12 | 44.44 |
| Grasp force | 18 | 1 | 5.55 | 1 | 5.55 | 5 | 27.78 | 11 | 61.11 |

3. Average reacting time of patients with cervical vertebra, lumbar vertebra, and rheumatism diseases: shown in Tab. 7

TABLE 7

| | the average reacting time of two patients groups (days) | | | | | | | |
|---|---|---|---|---|---|---|---|---|
| Groups | Case numbers | 1 day | 2 days | 3 days | 4 days | 5 days | >5 days | Average reacting time (days) X ± SD |
| cervical vertebra and lumbar vertebra diseases | 26 | 11 | 5 | 5 | 0 | 3 | 3 | 2.65 ± 2.29 |
| rheumatic diseases | 25 | 9 | 2 | 2 | 1 | 3 | 8 | 4.84 ± 4.53 |

4. Average onset time of taking effect on pains in cervical vertebra, lumbar vertebra diseases and rheumatism diseases are 10±4.81 days and 10.26±4.35 days, respectively.

5. The laboratory index has no significant changes. Among 30 patients observed, only 4 show erythrocyte sedimentation rate declined, and 4 show changes into negative result in anti-streptolysin "O" test. No changes for C reactive protein before and after the treatment. No changes in the rheumatoid agglutination test.

Adverse reactions: no adverse reactions observed among 60 treated patients.

CONCLUSIONS

During the clinical trials for treating cervical vertebra, lumbar vertebra diseases and rheumatism diseases, 30 patients respectively with cervical vertebra, lumbar vertebra diseases and rheumatic diseases are observed. The effects are observed by comparison with the patient himself before treatment. In conclusion, among the patients with cervical vertebra and lumbar vertebra diseases, the percentage of recovery and apparent effectiveness is 13.33%, percentage of effectiveness is 63.33%; the average reaction time is 2.65±2.29 days; and the average onset time is 10±4.81 days. Among the patients of rheumatic diseases, the percentage of recovery and apparent effectiveness is 13.33%; percentage of effectiveness is 46.67%; the average reaction time is 4.84±4.53 days; and the average onset time is 10.26±4.35 days. During the whole observation, the main symptoms of each disease are mainly observed, and other subordinate symptoms are observed secondarily. It can be observed that the device of the present invention has preferable clinical effects on pains with no adverse reactions observed during the observation period.

Stage II: Clinical Trials of Spatial Field Effect Physical Therapy Device for Treating Ordinary Diseases Objective: to explore the indications, contraindications, curative effects and adverse reactions of the device according to present invention.

General statistics: 100 patients were randomly selected from clinic service. The types of diseases and patients numbers are shown in the following table. All of these patients were in conformity with the criteria for selection. Among them, 34 were male and 66 were female with age of 15 to 86 year old, and the average age was 53.2 year old.

Course of Diseases for the Patients:

Selection for Patients

I. inclusion criteria: all the patients are in conformity with the diagnosis criteria for specialized diseases;

II. Exclusion Criteria:
   i. one of age <15 or >86 years old;
   ii. One with the primary severe pathological changes in brain, kidney, respiratory system, or hematopoietic system;
   iii. One with mental disorder or malignant tumor;
   iv. Female in pregnancy or lactation period;
   v. One who does not cooperate with the therapy.

III. Contraindications: the Above ii, iii, and iv in Criteria for Exclusion are Listed as Contraindications.

Treatment method: the device was in contraposition to the sites of pain or pathologic changes, with the distance of 10–30 cm between the device and body surface. The device was used for treatment for 10-20 days as a course of treatment, once one day, and 20-30 minutes every time. The patient for treatment were divided into heating group (in combination with ultra-infrared thermal-electrical radiation device) or un-heating group. During treated with the devices, it was required to stop all the drugs for treating the related diseases and other kinds of treatments.

Observation of the Curative Effects:

Observe the amelioration of related symptoms and signs, and the onset time of taking effect on the main symptoms during the treatment. The symptoms and signs of each kind of disease were divided into 6 grades by the observer, i.e., 0, ±, +, ++, +++, ++++, respectively.

Criteria for the Curative Effects:

1. apparent effective: the grade of the symptoms or signs is ameliorated with 2 degrees or more than 2 degrees after treatment;
2. effective: the grade of the symptoms or signs is ameliorated with 1 degree after treatment;
3. noneffective: no amelioration of the symptoms or signs after treatment.

Results of the Treatments:

1. The types of diseases, patient numbers, and the curative effects are shown in Table. 8:

| Case numbers | ≤1 months | | ≤half a year | | ≤1 years | | ≤5 years | | ≤10 years | | >10 years | |
|---|---|---|---|---|---|---|---|---|---|---|---|---|
| | N | (%) | N | (%) | N | (%) | N | (%) | N | (%) | N | (%) |
| 100 | 22 | 22 | 19 | 19 | 15 | 15 | 25 | 25 | 9 | 9 | 10 | 10 |

TABLE 8 the comparisons of types of diseases, patient numbers and the curative effects

| Serial number | Types of diseases | Case numbers | Apparently effective numbers | Effective numbers | Noneffective numbers |
|---|---|---|---|---|---|
| 1 | Cervical vertebra disease | 23 | 6 | 10 | 7 |
| 2 | Lumbar vertebra disease | 16 | 3 | 10 | 3 |
| 3 | Osteoarthritis in the knee joints | 14 | 1 | 10 | 3 |
| 4 | Trauma | 9 | 5 | 3 | 1 |
| 5 | Rheumatic & rheumatoid arthritis | 8 | 3 | 4 | 1 |

TABLE 8-continued the comparisons of types of diseases, patient numbers and the curative effects

| Serial number | Types of diseases | Case numbers | Apparently effective numbers | Effective numbers | Noneffective numbers |
|---|---|---|---|---|---|
| 6 | Acute and chronic soft tissue injury | 5 | 3 | 2 | / |
| 7 | Sequela for Cerebrovascular lesion | 5 | / | 2 | 3 |
| 8 | Pelvic inflammation | 4 | / | 4 | / |
| 9 | Periarthritis of shoulder | 3 | 2 | / | 1 |
| 10 | Menoxenia | 2 | 2 | / | / |
| 11 | Urinary system infection | 2 | 1 | 1 | / |
| 12 | Epigastric pain | 1 | 1 | / | / |
| 13 | Hordeolum | 1 | 1 | / | / |
| 14 | Facial nerve inflammation | 1 | 1 | / | / |
| 15 | Herpes zoster | 1 | 1 | / | / |
| 16 | Chronic fatigue syndrome | 1 | 1 | / | / |
| 17 | Benign prostatic hyperplasia | 1 | / | 1 | / |
| 18 | Lymphadenitis | 1 | / | 1 | / |
| 19 | Diabetes mellitus | 1 | / | 1 | / |
| 20 | Thrombus of lower limb vein | 1 | / | 1 | / |

2. The comparison of curative effects between heating and un-heating groups

| | Case Numbers | percentage of apparent effectiveness | percentage of effectiveness | percentage of noneffectiveness |
|---|---|---|---|---|
| un-heating | 24 | 12.5% | 66.7% | 20.8% |
| Heating | 76 | 32.9% | 46.1% | 21% |

3. The percentage of apparent effectiveness for heating and un-heating groups is total 28%, of effectiveness is 51%. Hence, the total percentage of effectiveness and apparent effectiveness is 79%. The percentage of noneffectiveness is 21%. See Tab. 10.

TABLE 10 the comparison of the total curative effects

| Case | Percentage of apparent effectiveness | | Percentage of effective-ness | | Total percentage of effectiveness | | percentage of non-effectiveness | |
|---|---|---|---|---|---|---|---|---|
| Numbers | N | % | N | % | N | % | N | % |
| 100 | 28 | 28 | 51 | 51 | 79 | 79 | 21 | 21 |

4. Onset time of taking effect: the shortest onset time of taking effect is 1 time after treatment, and the longest is 15 times after treatment, and the average onset time is 4.3 times.

Adverse reactions: no obvious adverse reactions are observed among the 100 tested patients. Only 5 felt slight dizzy and recovered quickly without any special treatment.

CONCLUSIONS

During this clinical trial, 100 patients were observed. The effects are observed by comparison with the patient himself before treatment. In conclusion, the percentage of apparent effectiveness is 28%, the percentage of effectiveness is 51%, and therefore the total percentage of effectiveness is 79%. The percentage of noneffectiveness is 21%. Wherein, in heating group, the percentage of apparent effectiveness is 32.9%, the percentage of effectiveness is 46.1%, the total percentage of effectiveness is 79%, and the percentage of noneffectiveness is 21%. In un-heating group, the percentage of apparent effectiveness is 12.5%, the percentage of effectiveness is 66.7%, and the total percentage of effectiveness is 79.2%, and the percentage of noneffectiveness is 20.8%. Average onset time is 4.3 times and average treatment time is 19.6 times.

The device according to the present invention has preferable curative effects on alleviating pains, and ameliorating local swelling and dysfunction. No adverse reactions are shown during the observation period. Only 5% of the tested patients felt slight dizzy during treating the diseases in the upper part of body, and afterwards recovered quickly without any special treatment.

Stage III: Clinical Trials of Spatial Field Effect Physical Therapy Device for Treating Pains in Cervical Vertebra and Lumbar Vertebra Diseases, Rheumatic and Rheumatoid Diseases General statistics: 35 patients were randomly selected from clinic service and hospitalization service, among which there were 19 patients with cervical vertebra and lumbar vertebra diseases, and 16 patients with rheumatic and rheumatoid diseases. All of these patients were in conformity with the criteria for selection. 8 of 19 patients with cervical vertebra and lumbar vertebra diseases were male and 11 of 19 were female at the age of 26-77 years old, and the average age was 56.6 years old. 1 of 16 with rheumatic and rheumatoid diseases were male and 15 of 16 were female at the age of 32-66 years old, and the average age was 47.5 years old.

Course Distribution of the Patients:

| Groups | Case numbers | ≦1 months N | (%) | ≦6 months N | (%) | ≦1 years N | (%) | ≦5 years N | (%) | ≦10 years N | (%) | >10 years N | (%) |
|---|---|---|---|---|---|---|---|---|---|---|---|---|---|
| cervical vertebra and lumbar vertebra diseases | 19 | 3 | 15.8 | 5 | 26.3 | 2 | 10.5 | 3 | 15.8 | 5 | 26.3 | 1 | 5.3 |
| rheumatic and rheumatoid diseases | 16 | / | / | 2 | 12.5 | 4 | 25 | 2 | 12.5 | 4 | 25 | 4 | 25 |

Wherein, the longest course of cervical vertebra and lumbar vertebra diseases was 11 years, and the shortest was one month. The average course was 3.8 years;

the longest course of rheumatic and rheumatoid diseases was 20 years, and the shortest was 5 months. The average course was 6.7 years.

Treatment times: 20 times for each patient.

Onset time of taking effects: among the patients being treated effectively, the shortest onset time is 1 day, the longest is 10 days, and the average onset time is 4 days.

Selection for Patients:

I. inclusion criteria: all the patients were in conformity with the diagnosis criteria for specialized diseases;

II. exclusion criteria:

i. one of age <15 or >86 years old;

ii. one with the primary severe pathological changes in brain, kidney, respiratory system, or hematopoietic system;

iii. one with mental disorder or malignant tumor;

iv. female in pregnancy or lactation period;

v. one who does not cooperate with the therapy.

III. contraindications: the above ii, iii, and iv in criteria for exclusion are listed as contraindications.

Treatment method: the device was also in contraposition to the sites of pain or pathologic change, while the difference from the above two stages was placing the device into the mattress of bed to form short-distance field instead of the long-distance field under the bed. The patients lay on the mattress. The upper field effect device was still placed over the patient body. Treat the patients with the device once a day, and 30-40 minutes every time. 20 days was a course of treatment. The effects were observed by comparison with the patient himself before treatment. There were 19 patients with cervical vertebra and lumbar vertebra diseases, and 16 with rheumatic and rheumatoid diseases. During treated by the present devices, it was required to stop all the antipyretic and antalgic drugs and other kinds of treatments.

Observation for the curative effects: further explore the clinical indications and contraindications of the present device; observe the amelioration of related symptoms or signs, and the onset time of taking effect on the main symptoms; record the adverse reactions.

Criteria for the Grades of Disease:

A. Criteria for the Grades of Symptoms of Cervical Vertebra and Lumbar Vertebra Diseases 1. Criteria for the Grades of Pains:

Grade I: no obvious pain in stillness or in movement;

Grade II: feel tolerable pain in normal movement having no influence on daily activities;

Grade III: feel intolerable pain in stillness having influence on daily activities.

2. Criteria for the Grades of Dysfunction:

Grade I: feel tired sometimes in the sites of pathologic changes, no pain during daily activities, assistance is required when changing posture, and diagnosis of dysfunction is negative;

Grade II: feel mild pain at the beginning of the movement. The pain continues with continuous movement, but disappears after rest. The movement of arthrosis or some local parts is slightly restrained;

Grade III: feel severe pain in movement, and the pain reduced somewhat in stillness, the movement is obviously restrained, swelling in local part or disfiguration of the arthrosis.

B. Criteria for the Grades of Pains Symptoms in Rheumatism

1. Tenderness in the Joints:

Grade I: feel no tenderness, but feel tenderness during stress or maximum passive movement;

Grade II: feel tenderness during stress on the edge of the joints or touching the ligaments;

Grade III: feel tenderness and frown to express feeling of pain during stress. The movement is slightly restrained;

Grade IV: feel severe tenderness during stress. The passive movement is severely restrained.

2. Dysfunction:

Grade I: sometimes with heavy feeling, no pain during daily activities, and negative diagnosis of obvious dysfunction;

Grade II: feel mild pain in movement, but no pain after rest. The function of joints is slightly restrained;

Grade III: feel severe pain in movement and less pain in stillness. The function of the joints is obviously restrained.

3. morning stiffness: record the time of morning stiffness.

4. swelling:

Grade I: no swelling;

Grade II: slightly swelling, and clear apophysis nearby;

Grade III: the swelling is as high as the apophysis;

Grade IV: the swelling is higher than the apophysis which hinders the functions and activities of the joints.

Criteria for Evaluating the Curative Effects:

1. apparently effective: the grade of the symptoms is ameliorated with 2 grades or more than 2 grades after treatment;

2. effective: the grade of the symptoms is ameliorated with 1 degree after treatment;

3. noneffective: no amelioration of the symptoms after treatment.

Results of Treatment 1. curative effect on symptoms of cervical vertebra and lumbar vertebra diseases: shown in Tab. 11

TABLE 11 curative effect on symptoms of cervical vertebra and lumbar vertebra diseases

| Symptoms observed | Case numbers | apparently effective | | effective | | Noneffective | |
|---|---|---|---|---|---|---|---|
| | | N | (%) | N | (%) | N | (%) |
| Pain | 17 | 8 | 47 | 7 | 41.2 | 2 | 11.8 |
| Dysfunction | 17 | 6 | 35.3 | 7 | 41.2 | 4 | 23.5 |

2. curative effect on symptoms of rheumatic and rheumatoid arthritis diseases: shown in Tab.

TABLE 12 curative effect on symptoms of rheumatic and rheumatoid arthritis diseases

| Symptoms observed | Case numbers | apparently effective | | effective | | Noneffective | |
|---|---|---|---|---|---|---|---|
| | | N | (%) | N | (%) | N | (%) |
| Pain | 16 | 9 | 56 | 4 | 25 | 3 | 19 |
| Dysfunction | 10 | 5 | 50 | 3 | 30 | 2 | 20 |
| Morning stiffness | 7 | 3 | 43 | 3 | 43 | 1 | 14 |
| Swelling | 3 | 1 | 33.3 | 2 | 66.7 | / | / |

3. The average onset time of taking effect on the pain in cervical vertebra, lumbar vertebra diseases and rheumatic and rheumatoid diseases are 3.15 days and 4.92 days, respectively.

Adverse Reactions:

The field intensity of the spatial field effect physical therapy device used at this stage of clinical trial is stronger than that of the above two stages (the following is for the detail). It is cautious to be treated for the patients who are aged, weak in health, or with heart diseases.

Three patients with adverse reactions were observed during this stage of clinical trials: hemicrania appeared in one 73-year-old female patient after the first treatment; headache and dizzy appeared in one 47-year-old female patient after twice treatments; neither of the two patients finished 20 times of treatments, and therefore they were not included in the observation cases. We know that all the symptoms disappeared after ceasing the treatment for 2 days during the follow-up visit with the two patients. Another case with adverse reactions was a 54-year-old female patient with heart-flustration appeared after twice treatments, but disappeared after ceasing treating for two days. The patient continued to be treated without any adverse reactions, but obvious curative effects instead.

Discussion:

From the results of the above three stages of treatments, it can be concluded that: I. the effects of solid columns is stronger than hollow columns; II. the effects of heating is stronger than non-heating; and III. the effects of short-distance field is stronger than long-distance field. It is because of the continuous improvement of the technology and usage that the improvement of curative effects can be observed in the third stage in comparison with the first and second stage of treatment. The patients are willing to be treated by this device.

Furthermore, the delightful effects of the present device are the outstanding effects for relief of pains and amelioration of dysfunction.

It is cautious to be treated for the patients who are aged, weak in health, or with heart-flustration symptoms under high field intensity. The preventive measures are: I. shorten the treating time from the normal 30-40 minutes to 20 minutes per time; II. reduce the two short-distance cushion-shaped fields into one. According to the total cases observed, the percentage of the adverse reactions is about 6%. The symptoms of the adverse reactions will disappear quickly after ceasing the treatment, and no sequelae observed.

According to the three stages of clinical trials, we believe that the spatial field effect physical therapy device is an instrument with favorable curative effects, especially has preferable curative effects on cervical vertebra diseases, lumbar vertebra diseases, rheumatic and rheumatoid diseases.

VI. Curative Cases

Case 1:
Name: LU Xiurong  Sex: Female  Age: 62
Date of treatment: Oct. 10, 2002

Chief complaints: pain of the left lower limb for 11 years, and began to aggravate 2 weeks ago.

Medical history to present: pain of the left lower limb for 1 year, and aggravating 2 weeks ago because of heavy labor, movement restrained, and numbness in the lateral left lower limb.

Examination: tenderness in the left lateral lumbar vertebra$_4$ and lumbar vertebra$_5$, positive result in the left straight-leg raising test, no obvious atrophy in the muscles of left lower limb.

X-ray examination: degenerative lesion in lumbar vertebra.

Diagnosis results: lumbar vertebra disease.

The patient was treated with spatial field effect physical therapy device with 30 minutes per time. The patient felt much less pain after the first time of treatment. After 6 times of treatment, the patient felt almost no pain and can move more freely than before with less numbness. After 15 times of treatment, the patient felt all symptoms disappeared. After 20 times of treatment, the patient fully recovered.

Case 2:
Name: ZHAO Da  Sex: Male  Age: 39
Date of treatment: Sep. 17, 2001

Chief complaints: pains in both knees of lower limbs for 1 year.

Medical history to present: pains in both knees of lower limbs for 1 year, swelling in local parts, and movement restrained, with positive diagnosis of rheumatoid arthritis. After many kinds of treatments, the symptoms had been slightly ameliorated, but pain still existed in both knees and limped obviously.

Examination: swelling in both knees and slightly red in the local parts.

Chemical examination: positive result of rheumatoid factor, and 38 mm/h of Erythrocyte sedimentation rate.

Diagnosis results: rheumatoid arthritis.

The patient was treated with spatial field effect physical therapy device with 30 minutes per time. The pain in both knees obviously ameliorated after 12 times of treatment, and limping was also ameliorated. After 15 times of treatment, the pain almost disappeared. After 20 times of treatment, the patient could almost walk freely and could go shopping. The Erythrocyte sedimentation rate was 22 mm/h after treatment.

---
Case 3:
Name: JIANG Li   Sex: Female   Age: 56
Date of treatment: Sep. 15, 2000
---

Chief complaints: muscle pain all over the body for 18 years, and began to aggravate 1 month ago.

Medical history to present: muscle pain all over the body lasts for 18 years. Diagnosis result is fibromyalgia syndrome. The alleviation and aggravation of the symptoms alternate after many kinds of treatments of traditional Chinese medicine and western medicine. The symptom aggravated without any obvious cause 1 month ago, especially in medial thighs of both lower limbs, with muscle trembling. It was difficult for the patient to stand.

Examination: many rather hard nods with the size similar to peanut could be touched in the medial thighs of both lower limbs with slight tenderness and good activity.

Diagnosis results: fibromyalgia syndrome.

The patient was treated with spatial field effect physical therapy device with 30 minutes per time and felt less pain after 2 times of treatment. The symptoms exacerbated to the original level after the 4$^{th}$ treatment. After continuous treatment up to 10 times, the symptoms ameliorated gradually day by day. The patient felt pain ameliorated, and looked much better. After 15 times of treatment, the nods in the medial thighs became soft and small, and the tenderness disappeared. The patient felt in the best state since 18 years of illness.

---
Case 4:
Name: WANG Rong   Sex: Male   Age: 62
Date of treatment: Oct. 5, 2002
---

Chief complaints: pain and discomfort in the joints of the right knee for 1 year, and began to aggravate 1 week ago.

Medical history to present: The patient felt pain in the joints of the right knee before 1 year and felt weak in the legs. It was difficult to go up and down stairs. The movement in local part was restrained.

Diagnosis result is "degenerative osteoarthritis of right knee". The above symptoms became aggravated 1 week ago because of excessive movement. When he went upstairs, the feet of the patient could not entirely touch the ground and could not without armrest.

X-ray examination: degenerative osteoarthritis of right knee.

Diagnosis results: osteoarthritis of right knee.

The patient was treated with spatial field effect physical therapy device with 30 minutes per time and felt less pain in the local parts after 2 times of treatment. After 8 times of treatment, the patient could go upstairs to the 4$^{th}$ floor with his feet entirely touching on the ground. After continuous treatment to 12 times, almost no symptoms appeared, and after 20 times, the patient completely recovered.

---
Case 5:
Name: CHE Xueru   Sex: Female   Age: 77
Date of treatment: Aug. 7, 2002
---

Chief complaints: discomfort in shoulder and neck for 2 months.

Medical history to present: discomfort in shoulder and neck 2 months ago, the movement in the shoulder restrained, unable to hold things, especially in the left lateral. Numbness was also in all the limbs.

Examination: cervical vertebra curve straightened with tenderness of the paracervical area, and positive diagnosis results for both brachial plexus distraction test and cervical traction test.

X-ray examination: cervical vertebra disease.

Diagnosis results: cervical vertebra disease, shoulder-neck syndrome.

The patient was treated with spatial field effect physical therapy device with 30 minutes per time. Patient felt less pain in shoulder and neck and less numb in all the limbs after 5 times of treatment. After 10 times of treatment, the patient could hold things. After continuous treatment to 18 times, almost no symptoms existed. After 20 times of treatment, the patient completely recovered.

What is claimed is:

1. A spatial field effect physical therapy device, characterized in that it comprises a base and 64 equidistant Yijing columns fitted vertically on the same in the form of a square array by 8 rows and 8 columns, wherein each Yijing column is at a height of 2 to 18 unit length, and the sum height of two diagonal Yijing columns of a rectangle formed by any 4 columns in the square array is equal to that of the other two diagonal columns.

2. The spatial field effect physical therapy device according to claim 1, characterized in that the Yijing columns at the four corners of the square array are higher than others, respectively at the height of 16, 17, 18, and 17 unit length.

3. The spatial field effect physical therapy device according to claim 2, characterized in that the space between two neighbouring Yijing columns is between ⅓~½ of the Yijing columns' diameter.

4. The spatial field effect physical therapy device according to claim 3, characterized in that the Yijing columns are metal columns.

5. The spatial field effect physical therapy device according to claim 4, characterized in that the Yijing columns are solid columns.

6. The spatial field effect physical therapy device according to claim 5, characterized in that it further comprises a transparent mask on the base which covers all the Yijing columns.

7. The spatial field effect physical therapy device according to claim 4, characterized in that the Yijing columns are hollow columns.

8. The spatial field effect physical therapy device according to claim 7, characterized in that it further comprises a transparent mask on the base which covers all the Yijing columns.

9. The spatial field effect physical therapy device according to claim 4, characterized in that it further comprises a transparent mask on the base which covers all the Yijing columns.

10. The spatial field effect physical therapy device according to claim 3, characterized in that it further comprises a transparent mask on the base which covers all the Yijing columns.

11. The spatial field effect physical therapy device according to claim 2, characterized in that it further comprises a transparent mask on the base which covers all the Yijing columns.

12. The spatial field effect physical therapy device according to claim 1, characterized in that it further comprises a transparent mask on the base which covers all the Yijing columns.

* * * * *